(12) United States Patent
Sale et al.

(10) Patent No.: US 6,599,126 B1
(45) Date of Patent: Jul. 29, 2003

(54) METHOD AND APPARATUS FOR WHITENING TEETH USING A FLUID DELIVERY TOOTHBRUSH

(75) Inventors: David W. Sale, Heber Springs, AR (US); Scott Stephen Bradshaw, Cabot, AR (US)

(73) Assignee: Professional Dental Technologies, Inc., Batesville, AR (US)

(*) Notice: Subject to any disclaimer, the term of this patent is extended or adjusted under 35 U.S.C. 154(b) by 0 days.

(21) Appl. No.: 09/474,489

(22) Filed: Dec. 29, 1999

Related U.S. Application Data

(60) Provisional application No. 60/114,505, filed on Dec. 31, 1998.

(51) Int. Cl.$^7$ .............................................. A61C 13/08
(52) U.S. Cl. ...................................................... 433/216
(58) Field of Search ........................... 433/80, 216, 82, 433/84, 85, 215

(56) References Cited

U.S. PATENT DOCUMENTS

| | | | | |
|---|---|---|---|---|
| 1,573,749 A | * | 2/1926 | Ross, Jr. ........................ | 433/80 |
| 2,140,307 A | * | 12/1938 | Belaschk et al. | |
| 2,841,806 A | * | 7/1958 | Blasi | |
| 3,195,537 A | * | 7/1965 | Blasi | |
| 3,389,468 A | * | 6/1968 | Lewis et al. .................... | 433/80 |
| 3,418,329 A | | 12/1968 | Robert et al. | |
| 3,977,084 A | * | 8/1976 | Sloan | |
| 4,743,199 A | * | 5/1988 | Weber et al. ................. | 433/216 |
| 5,032,178 A | | 7/1991 | Cornell | |
| 5,076,791 A | | 12/1991 | Madray, Jr. | |
| 5,098,303 A | | 3/1992 | Fischer | |
| 5,128,122 A | | 7/1992 | Cerami et al. | |
| 5,142,723 A | * | 9/1992 | Lustig et al. ................. | 15/22.1 |
| RE34,196 E | | 3/1993 | Munro | |
| 5,234,342 A | | 8/1993 | Fischer | |
| 5,290,566 A | | 3/1994 | Schow et al. | |
| 5,301,381 A | * | 4/1994 | Klupt ........................... | 15/22.1 |
| 5,376,006 A | | 12/1994 | Fischer | |
| 5,378,153 A | * | 1/1995 | Giuliani et al. .............. | 433/216 |
| 5,409,631 A | | 4/1995 | Fischer | |
| 5,425,953 A | | 6/1995 | Sintov et al. | |
| 5,500,207 A | | 3/1996 | Goulet | |
| 5,573,398 A | * | 11/1996 | Towle et al. .................... | 433/80 |
| 5,611,687 A | * | 3/1997 | Wagner ........................ | 433/80 |
| 5,611,690 A | | 3/1997 | Summers et al. | |
| 5,631,000 A | | 5/1997 | Pellico et al. | |
| 5,645,428 A | | 7/1997 | Yarborough | |
| 5,648,064 A | | 7/1997 | Gaffar et al. | |
| 5,658,148 A | * | 8/1997 | Neuberger et al. ........... | 433/215 |
| 5,718,886 A | | 2/1998 | Pellico | |
| 5,725,843 A | | 3/1998 | Fischer | |
| 5,746,598 A | | 5/1998 | Fischer | |
| 5,759,038 A | | 6/1998 | Fischer | |
| 5,766,011 A | | 6/1998 | Sibner | |
| 5,766,574 A | | 6/1998 | Christina-Beck et al. | |
| 5,770,105 A | | 6/1998 | Fischer | |
| 5,770,182 A | | 6/1998 | Fischer | |
| 5,779,471 A | * | 7/1998 | Tseng et al. ................... | 433/80 |
| 5,814,304 A | | 9/1998 | Wong et al. | |
| 5,921,251 A | * | 7/1999 | Joshi ........................... | 433/216 |
| 6,056,548 A | * | 5/2000 | Neuberger et al. ........... | 433/216 |

OTHER PUBLICATIONS

A New Era in Whitening Systems, Dentistry Today, Dec. 1998, vol. 17, No. 12.
Opalescence® Whitening Toothpaste, by Ultradent Products, Inc., 1998.
White & Brite® Omnii Ultimate 16™ Tooth Whitening System.
Rembrandt Bleaching Gel Plus 10%, 15%, & 22%, Instructions for Dentists, Rembrandt®.
Your at–Home Tooth Whitening Program, Rembrandt®.

* cited by examiner

*Primary Examiner*—Ralph A. Lewis
(74) *Attorney, Agent, or Firm*—William J. Sapone; Coleman Sudol Sapone, P.C.

(57) ABSTRACT

A method and apparatus are provided for whitening teeth using a fluid delivery toothbrush to deliver a bleaching liquid to the teeth during brushing. The fluid delivery toothbrush may be manual or powered, delivering fresh relatively high strength bleaching liquid to the tooth surfaces, preferably on a daily basis, for one to three minutes.

4 Claims, 4 Drawing Sheets

FLUTED BRUSH

PATH IN-BETWEEN
THE BRUSH FIBERS

BRUSH

PATH THROUGH
THE BRUSH FIBERS

METHOD AND APPARATUS FOR WHITENING TEETH USING A FLUID DELIVERY TOOTHBRUSH

CROSS-REFERENCE TO RELATED APPLICATIONS

This invention claims priority in U.S. Provisional Patent Application No. 60/114,505 filed Dec. 31, 1998.

TECHNICAL FIELD

This invention relates to a method and apparatus for bleaching teeth using a fluid delivery dental brush to work a bleaching composition into a tooth surface.

BACKGROUND

Dental health is generally dependent on a program of brushing, flossing and periodic dental office visits. However, the maintenance of good dental health may not be evident because of tooth staining, for example from smoking or heavy coffee drinking. Brushing and office cleanings alone cannot address this problem.

One method for whitening teeth utilizes bleaching. During an office visit, a patient can have a composition such as hydrogen peroxide applied to the teeth, the gum tissue protected by a rubber dam, with heat applied to the composition. Such a treatment may last for from 30 minutes to one hour and many such treatments are necessary to achieve a sufficient color improvement.

Another method uses an impression of the teeth to form a tray that holds the bleaching agent. The patient places the tray with the bleaching agent in the mouth and keeps this on the teeth for several hours or even overnight, with the agent changed about every 2 hours. Of course, the extended time during which the tray must be maintained in the mouth is both inconvenient and uncomfortable.

In U.S. Pat. Nos. 5,098,303, 5,376,006 and 5,234,342, a high viscosity bleaching agent is used with a tray configured to cover a patients' tooth surfaces, the bleaching agent placed in a matrix material of high viscosity and low saliva solubility to hold the bleaching agent in contact with the tooth surfaces for greater than 2 hours. The viscous tray bleaching composition holds the bleaching agent on the tooth surfaces as well as the tray on the teeth.

However, this bleaching method still requires substantial time during which a.patient must keep a tray in the mouth. In addition, these are all passive processes, that is, the agent simply contacts the tooth surface, and as time goes on the activity of the composition in contact with the tooth surface decreases, reducing effectiveness.

SUMMARY OF THE INVENTION

It is an object of the present invention to provide a method for tooth whitening that avoids the use of trays.

It is a further object of the present invention to provide a method for tooth whitening that avoids use of viscus or gelled bleaching compositions.

It is a further object of the present invention to provide a bleaching method that obtains tooth whitening by bleaching the tooth surfaces during or after normal tooth brushing.

These and other objects of the present invention are achieved by providing a fluid delivery toothbrush that provides a mechanical brushing action for tooth cleaning, providing a brush for the fluid delivery toothbrush adapted for incorporating a liquid therein, providing a liquid tooth bleaching composition and delivering the liquid tooth bleaching composition during tooth brushing so that the mechanical action of the brush on the tooth surface promotes surface contact of the bleaching agent on the scrubbed tooth surfaces.

Utilizing the applicant's invention, the bleaching reaction is promoted as the mechanical action of the brush assures active contact with the tooth surface such that fresh high strength bleaching agent is not only deposited, but also worked into and on the tooth surface to promote more effective bleaching. In addition, when combined with normal brushing, multiple short length treatments are provided as opposed to several massive tray treatments, substantially increasing convenience while increasing effectiveness. In addition, such frequent treatments result in prompt action on fresh stains to reduce the time the staining agent has to act, promoting long term maintenance and possibly reducing the need for "touch-up" or periodic in-office maintenance bleaching treatment. Thus, the invention is a major advance in the art.

DETAILED DESCRIPTION OF THE INVENTION

Figure 1:
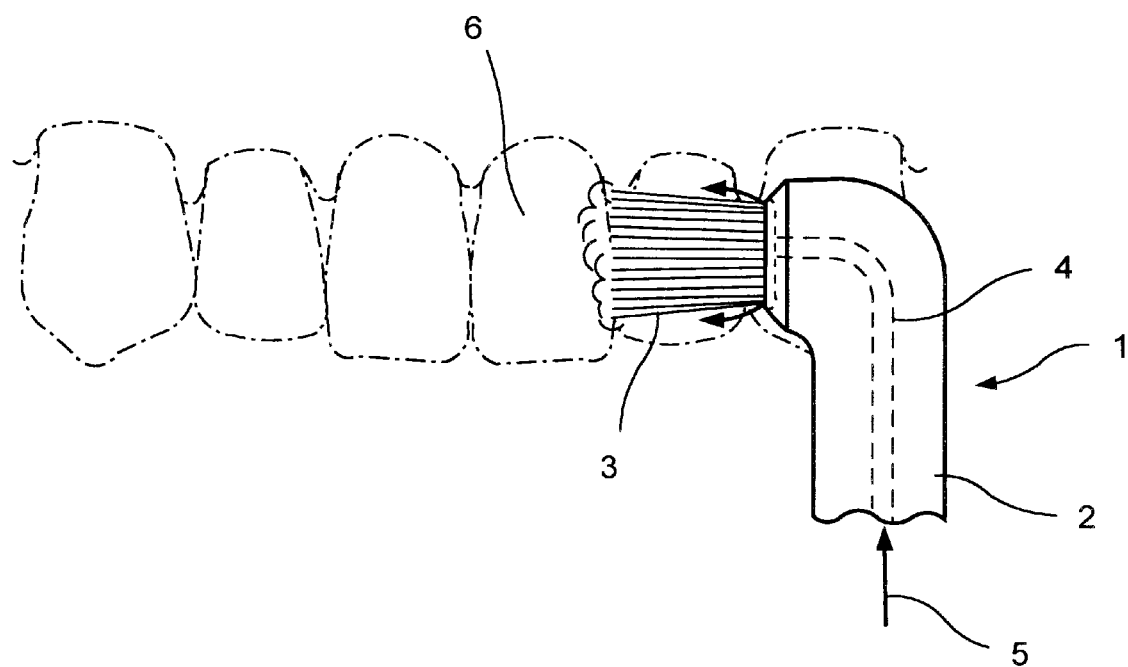
FIG. 1 is a view illustrating the method of the present invention.

The invention is a method for tooth whitening that utilizes a fluid delivery toothbrush for scrubbing a tooth surface, a brush provided on the fluid delivery toothbrush having bristles that work a bleaching solution into and on the tooth surface. Preferably, the brush is either impregnated with a bleaching agent or is adapted to receive and deliver a bleaching liquid to the tooth surface during brushing. In a preferred embodiment, the bleaching liquid is contained in a fluid reservoir in proximity to the brush to facilitate delivery of the bleaching agent during brushing. Also preferred is the use of a powered fluid delivery toothbrush to increase mechanical action on the tooth surface and thereby further improve bleaching effectiveness.

The term "fluid delivery toothbrush" means a toothbrush that has bristles for scrubbing a tooth surface and means, internal or external, for delivering a fluid during brushing.

The term "powered toothbrush" means a toothbrush that has a motor or other means to drive a brush having bristles for rotation, oscillation, or vibration, which each effect at least a mechanical scrubbing of the tooth surface, in addition to the hand movements of the user.

Mechanical action whether by manual or powered brushing provides several benefits. First, it cleans the tooth surface of debris, plaque or other material which would interfere with a bleaching action by preventing direct surface contact. Bleaching involves a reaction between a bleaching agent and the staining agent and if physical matter precludes contact, no bleaching will occur.

The mechanical action also distributes the bleaching agent over the tooth surface and works the bleaching agent into the surface. Staining agents typically may not only be on the tooth surface but may penetrate to a certain degree into a top layer of the tooth surface, and for the bleaching to be effective, the bleaching agent must similarly penetrate into the top layer. By working the bleaching agent over the tooth surface, the effective contact for reaction is maximized as the fluid is constantly refreshed to maintain high reactivity. Each sweep of the brush bristles removes old fluid and applies fresh fluid to promote maximum effectiveness in bleaching.

The mechanical action also promotes efficiency in that it forces the bleaching fluid into the interstices between the teeth as well as on the more accessible front and rear tooth surfaces.

In addition to the mechanical action, frequency of bleaching is also an important aspect of the method of the invention.

The method of bleaching is undertaken during or after regular brushing, with the same toothbrush used for routine tooth cleaning. Thus, multiple short term, i.e., one to three minute, treatments are effected on at least a daily basis as opposed to the two or more hour treatments done typically every three to six months in a dental office or daily for several hours at home over a 1–2 week period. While a single short term treatment may be of little value in whitening, the progressive short term treatments effectively eliminate ongoing stain build-up and incrementally improve whitening such that after about two months, optimum whiteness is achieved and thereafter maintained.

While there are tooth whitening toothpaste formulas available, these integrate whiteners with tooth cleaning agents and by integrating, they reduce effectiveness. That is, the toothpaste formulation is primarily directed to abrasive action and contain other materials (such as foaming agents, etc.) for promoting mechanical cleaning and these materials may interact with the whitening compositions and certainly these pastes cannot deliver the higher potency liquid bleaching agents usable in accordance with the present invention which are typically highly reactive and difficult to incorporate with other materials. Thus, normal brushing with these whitening toothpaste's cleans the surface but any whitening agent is at low concentration, and must compete for surface contact with the cleaning agents and therefore cannot promote the effective whitening as is achieved by the present invention.

Referring to FIG. 1, a toothbrush 1 has a neck portion 2 with a brush 3 mounted on a forward portion thereof. The neck 2 has a passage 4 through which a fluid 5 may be delivered to the brush 3. The brush 3 contacts a tooth 6, spreading and working the fluid 5 into and over the tooth surface.

Figure 2:
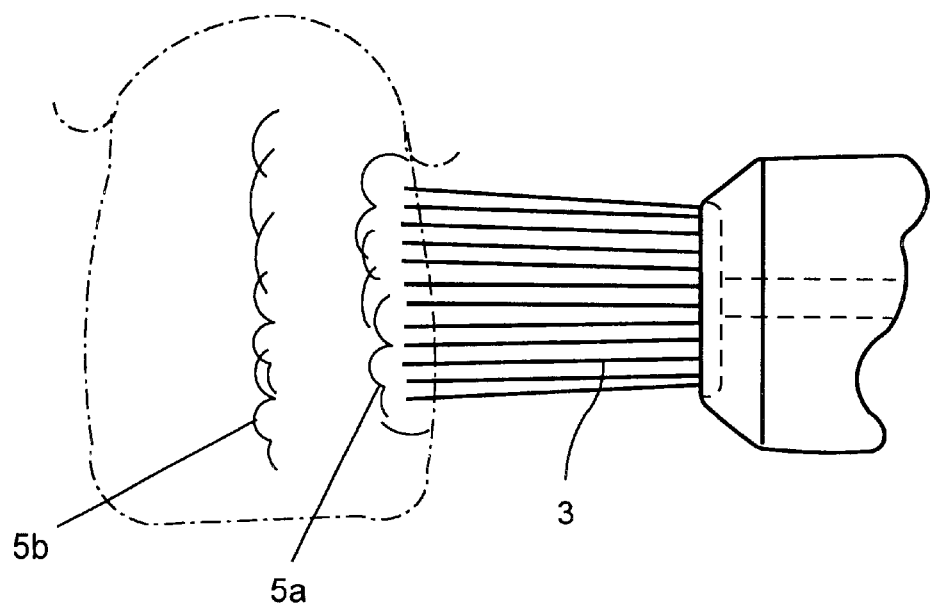
FIG. 2 is an enlarged view showing the active bleaching of a tooth surface.

As shown in FIG. 2, each pass of the brush 3 over the tooth surface not only scours the tooth surface but puts fresh fluid 5a over the surface, increasing the reactivity of the fluid with any straining agent while sweeping aside the prior fluid 5b which has diminished strength from prior reaction with staining agents.

Figure 3A:
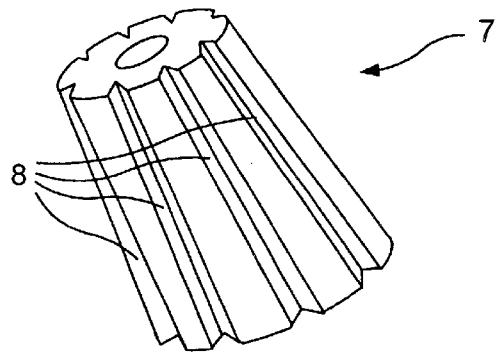
FIGS. 3a, b and c are views of preferred brushes usable in the present invention.
Figure 3B:
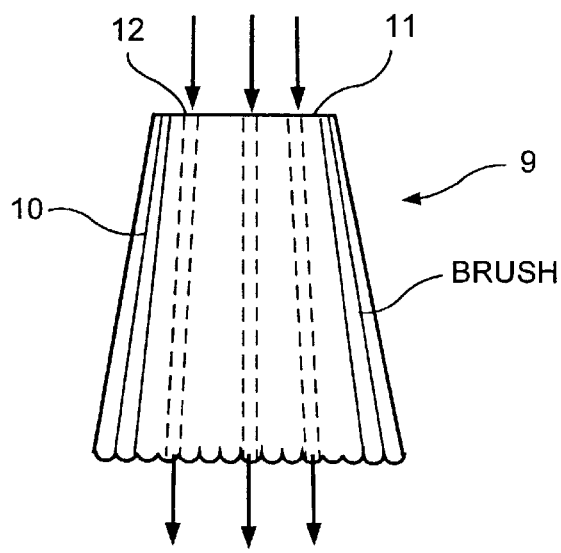
Figure 3C:
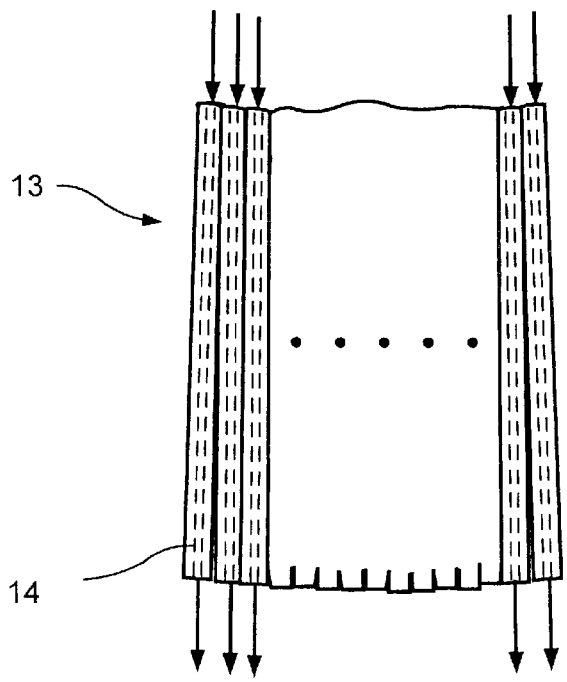

Referring to FIGS. 3a, 3b and 3c, several brush designs suitable for use with the present invention are shown. These are for illustration only and generally any brush design could be used so long as liquid is supplied during brushing.

FIG. 3a shows a brush 7 with flutes 8 in its sides that promote liquid flow along the sides to the brush tips. FIG. 3b shows a brush 9 having bristles 10 extending from a perforated base 11 having holes 12 through which liquid infiltrates the fibers. FIG. 3c shows a brush 13 with hollow fibers 14, the liquid passing through the fibers to the tooth surface.

Figure 4:
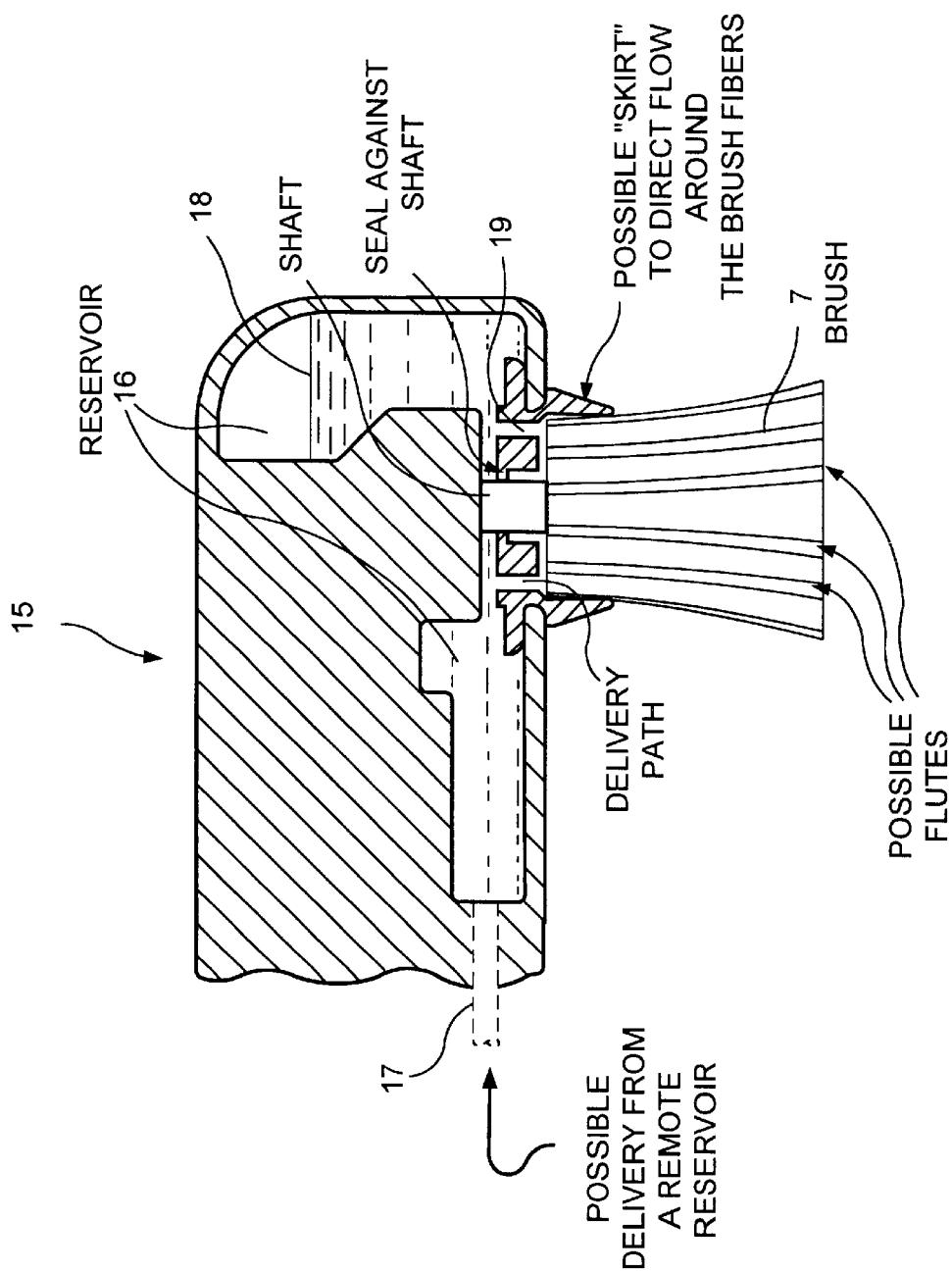
FIG. 4 is a cross-sectional view of a fluid delivery toothbrush usable in the present invention.

Referring to FIG. 4, a manual fluid delivery toothbrush 15, is shown. This again is for illustration only as other fluid delivery toothbrush designs are known.

The toothbrush 15 uses the fluted brush 7, liquid supplied from a reservoir 16 adjacent the brush. This reservoir can be connected via a passage 17 to a liquid source that is internal or external to the toothbrush 15. A liquid bleaching agent 18 is located in the reservoir and travels via gravity, capillary action or pressure differential through an opening 18 that leads to the brush. As one passes the brush over a tooth surface, the liquid bleaching agent is dispensed.

Figure 5:
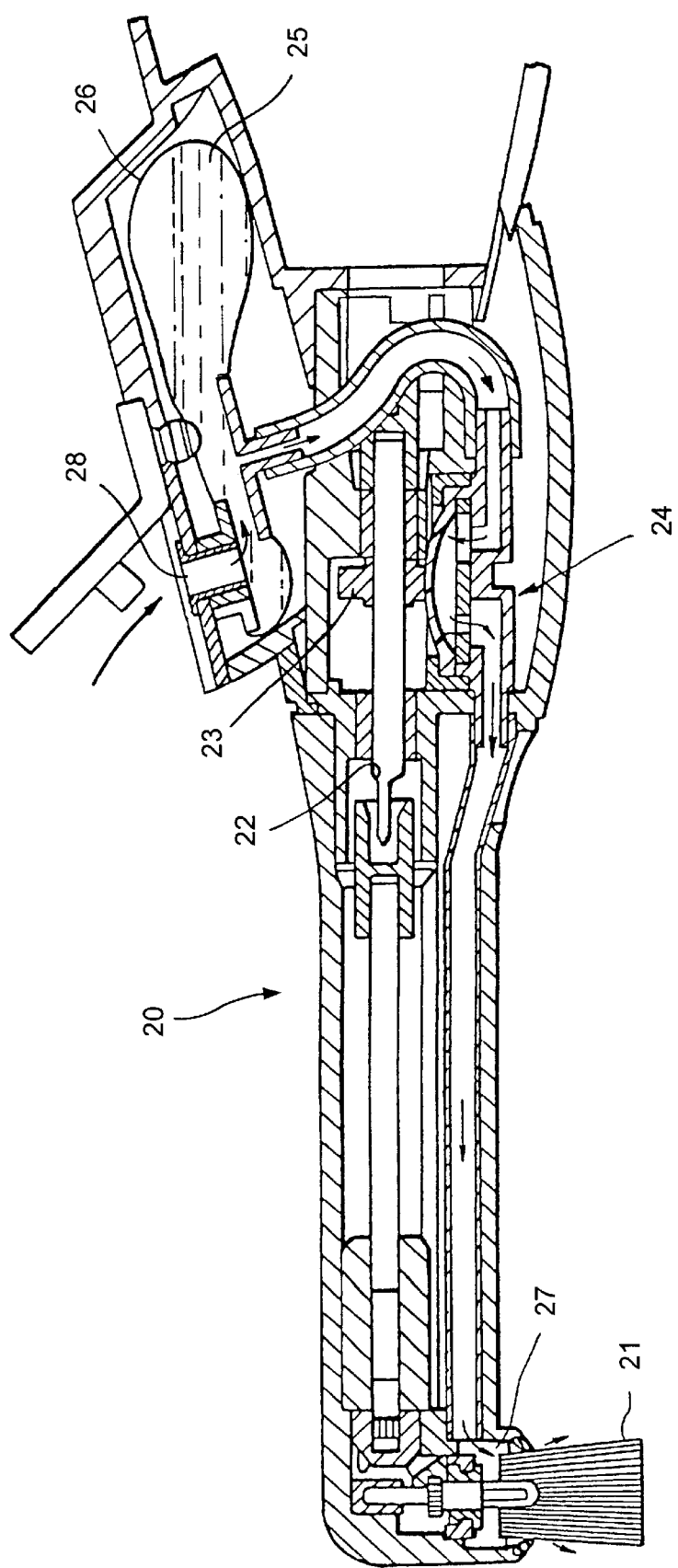
FIG. 5 is a cross-sectional view of an alternative fluid delivery toothbrush also usable with the present invention.

Referring to FIG. 5, a neck portion 20 of a powered toothbrush is shown. In this embodiment, rotary action is used to drive a brush 21. The neck contains a drive shaft 22 that has a cam 23 that acts on a pump 24 for delivering a fluid 25 located in a bladder 26 to a chamber 27 near the base of the brush. The brush can be any of those described previously. With such a neck, a liquid bleaching solution is delivered during rotation of the brush via a pumping action. The solution can be replenished through the opening 28.

In the preferred embodiment, a rotary toothbrush is used to apply the bleaching agent, as described in relation to FIG. 5. A preferred brush useful with the present invention is the one having an outer perimeter incorporating channels or flutes as shown in FIG. 3a that directs a liquid bleaching agent to the distal end of the brush. A fluid delivery toothbrush designed for fluid delivery such as that disclosed in U.S. patent application No. 09/328,619, filed Jun. 9, 1999 or U.S. Pat. Nos. 4,315,741 or 5,208,933, among others, may be used to apply the bleaching agent.

The bleaching agent must be in liquid form to maximize distribution over the tooth surface as well as to maximize activity. As the contact time is limited by the application method of the invention, higher concentration agents can be used as these will be flushed after the 1–3 min. treatment. A relatively thick or gel type bleaching agent would adhere to the surface and resist removal, and itself become an inhibitor of the reapplication of fresh high concentration bleaching agent. Such reapplication which is accomplished by the mechanical action of the brush on the tooth surface is an important consideration in promoting the bleaching action. Liquids are also more easily worked over the tooth surfaces and into the interstices between the teeth.

One usable bleaching liquid comprises hydrogen peroxide (0.5–10 more preferably 0.5 to 5%, by weight range), water, and a stabilizer. For example, a 3% hydrogen peroxide solution with 0.1–0.5% of a stabilizer may be used. Acetanilide or a similar organic material can also be used with a pyrophosphate stabilizer such as sodium acid pyrophosphate (0.1–1.0%) with a preferred amount of about 0.5%. Of course, virtually any bleaching liquid could be used with the present invention, preferably at somewhat higher active concentration to take advantage of the short term exposure of delicate tissue to the agent during brush bleaching which avoids aggravating the delicate tissue, a major problem with long exposure bleaching systems.

Utilizing the invention, effective tooth whitening is achieved, at home, without trays or viscous gels, and as part of a normal program to promote dental health. The application is convenient, short term, yet effective in obtaining overall tooth whiteness.

While preferred embodiments of the present invention have been shown or described, it will be understood that various changes or modifications can be made without varying from the scope of the present invention.

We claim:

1. A method for non-optically bleaching teeth consisting essentially of:
   a) providing a powered fluid delivery toothbrush having a brush and means for delivering a fluid to the brush, a reservoir for containing a non-abrasive bleaching liquid consisting essentially of a liquid peroxide and water, in fluid communication with the brush;
   b) placing the non-abrasive bleaching liquid in the reservoir;
   c) driving the brush for oscillation, rotation or vibration; and,
   d) treating the teeth for up to 3 minutes while driving the brush to scour the teeth while simultaneously delivering the bleaching liquid thereto, thereby increasing the reactivity of the bleaching liquid with any staining agent, the driven brush increasing mechanical action on the teeth during deposition of the bleaching liquid on the tooth surfaces;
   e) continuously delivering fresh bleaching liquid to the brush for spreading and working the bleaching liquid into and over the tooth surfaces to bleach the teeth; and,
   periodically repeating steps a–e.

2. The method of claim 1 wherein the bleaching liquid contains hydrogen peroxide.

3. The method of claim 1 further comprising:
   first brushing the teeth to remove particles prior to brushing the teeth with delivery of the bleaching liquid.

4. The method of claim 1 wherein the steps of the method for bleaching the teeth are repeated on a daily basis.

* * * * *